(12) United States Patent
Alruhaimi

(10) Patent No.: US 10,918,463 B1
(45) Date of Patent: Feb. 16, 2021

(54) BONY SCREW WITH MOVABLE BRACKET ARM

(71) Applicant: KING SAUD UNIVERSITY, Riyadh (SA)

(72) Inventor: Khalid Abdullah Ibrahim Alruhaimi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/882,496

(22) Filed: May 24, 2020

(51) Int. Cl.
*A61C 8/00* (2006.01)
*A61C 7/10* (2006.01)
*A61C 7/14* (2006.01)

(52) U.S. Cl.
CPC .............. *A61C 8/0022* (2013.01); *A61C 7/10* (2013.01); *A61C 7/146* (2013.01); *A61C 8/0074* (2013.01); *A61C 8/0096* (2013.01)

(58) Field of Classification Search
CPC ......... A61C 8/0022; A61C 7/10; A61C 7/146; A61C 8/0074; A61C 8/0096; A61C 8/0048; A61C 7/28; A61C 8/0063; A61C 8/0075; A61C 17/14
See application file for complete search history.

(56) References Cited

U.S. PATENT DOCUMENTS

| 3,721,005 | A | 3/1973 | Cohen |
| 3,925,893 | A | 12/1975 | Anderson |
| 4,842,518 | A | 6/1989 | Linkow et al. |
| 4,932,868 | A | 6/1990 | Linkow et al. |
| 5,921,774 | A | * 7/1999 | Kanomi .................... A61C 7/00 433/173 |
| 6,354,834 | B2 | * 3/2002 | Kanomi .................... A61C 7/00 433/173 |
| 6,592,366 | B2 | 7/2003 | Triaca et al. |
| 7,101,177 | B2 | 9/2006 | Lin |
| 9,320,577 | B1 | 4/2016 | Alotaibi et al. |
| 10,028,807 | B1 | * 7/2018 | Alruhaimi ................ A61C 7/28 |
| 10,357,341 | B2 | 7/2019 | Alruhaimi |
| 2002/0018978 | A1 | 2/2002 | Triaca et al. |
| 2004/0157187 | A1 | 8/2004 | Lin |
| 2006/0024644 | A1 | 2/2006 | Cohen |
| 2008/0293005 | A1 | 11/2008 | Rahlis et al. |
| 2010/0075271 | A1 | * 3/2010 | Sabilla .................... A61C 7/00 433/18 |

(Continued)

FOREIGN PATENT DOCUMENTS

FR 2936701 A1 4/2010

*Primary Examiner* — Matthew J Lawson
(74) *Attorney, Agent, or Firm* — Nath, Goldberg & Meyer; Richard C. Litman

(57) ABSTRACT

A bony screw with a movable bracket arm includes a head and a shank extending therefrom. The shank has an upper portion, a threaded lower portion adjacent to the upper portion, thereby defining a junction, and a self-tapping tip. An annular flange is disposed at the junction between the upper portion and the threaded lower portion of the shank, and is contiguous with respect to each of the upper and threaded lower portions, and has a peripheral surface with a diameter greater than a diameter of the head and greater than a diameter of the upper portion, thus defining a stop between the upper and threaded lower portions. A first end of a bracket arm is pivotally secured to the upper portion of the shank, and an opposed second end of the bracket arm defines a loop.

2 Claims, 4 Drawing Sheets

(56) References Cited

U.S. PATENT DOCUMENTS

| | | |
|---|---|---|
| 2010/0160920 A1 | 6/2010 | Mommaerts |
| 2012/0189985 A1 | 7/2012 | Iglesias |
| 2015/0250567 A1 | 9/2015 | Buddemeyer et al. |
| 2018/0132978 A1* | 5/2018 | Alruhaimi ............ A61C 8/0012 |
| 2018/0353230 A1 | 12/2018 | Marcus |

* cited by examiner

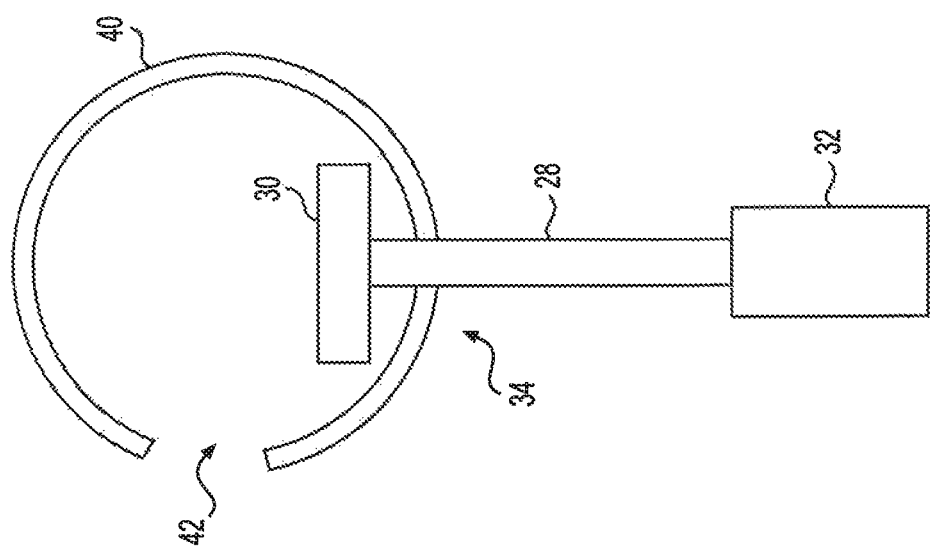

BONY SCREW WITH MOVABLE BRACKET ARM

BACKGROUND

1. Field

The disclosure of the present patent application relates to surgical screws and fasteners used in dentistry and maxillofacial orthopedics, and particularly to a bony screw with a movable bracket arm that has a bracket arm pivotally attached to, and extending outwardly from, the shaft or shank of the screw for supporting and facilitating the passage of a distractor bar of a distractor or other maxillofacial fixing and dental appliance.

2. Description of the Related Art

Fracture fixing devices and distraction devices typically require a strong holding plate bracket to grip the traction bar. The use of a strong holding plate bracket, however, requires the creation of a surgical flap. The creation of a surgical flap not only prolongs the time in which the patient spends in surgery, but it also lengthens the time necessary for recovery. A bone screw with a fixed shank, for example, further does not allow passage of the fixing bar through the brackets if multiple screws are fastened to the bone in different levels.

A tooth band bracket also typically cannot be used in cases where the selected teeth are too weak to hold the band bracket or when the investing bone level around the roots of the teeth is short or periodontally involved with reabsorbed bone around the roots of the selected teeth and not strong enough to withstand the forces of distraction and the anchor load exerted by the traction forces. Further, at times the stability of the tooth band bracket against the attraction forces of the moving bony segment may be a cause for concern. Additionally, the fixed bracket shank in these bands has the same issue of difficulty of passing the fixing bar through multiple brackets in different levels. Thus, a bony screw with a movable bracket arm solving the aforementioned problems is desired.

SUMMARY

The bony screw with a movable bracket arm is provided for supporting a distractor or other maxillofacial fixing and dental appliance. The bony screw with movable bracket arm includes a head and a tooth shank extending therefrom. As a non-limiting example, in order to facilitate fixation, the head may have cruciform slots defined therein; i.e., the head may be a Phillips head. The shank has an upper portion, a threaded lower portion adjacent to the upper portion, thereby defining a junction, and a self-tapping tip extending from the threaded lower portion. An annular flange is disposed at the junction between the upper portion and the threaded lower portion of the shank. The annular flange is contiguous with respect to each of the upper portion and the threaded lower portion, and has a peripheral surface with a diameter greater than a diameter of the head and greater than a diameter of the upper portion, thus defining a stop between the upper portion and the threaded lower portion.

A first end of a bracket arm is pivotally secured to the upper portion of the shank, and an opposed second end of the bracket arm defines a loop adapted for supporting a distraction osteogenesis bar. It should be understood that the pivotal connection may be provided by any suitable type of pivot. As a non-limiting example, a collar having a slot formed therethrough may be provided, such that the upper portion of the shank extends through the slot, with the first end of the bracket arm being disposed within the collar and being pivotally secured between the collar and the upper portion of the shank. The second end of the bracket arm is disposed external to the collar in this arrangement. The first end of the bracket arm may terminate in, for example, a short cylindrical rod, a rolled cylindrical sheet, etc. In order to properly position and support the distraction osteogenesis bar, or other maxillofacial fixing and dental appliance, the second end of the bracket arm may extend beyond the peripheral surface of the annular flange (i.e., the radial component of the length of the bracket arm is greater than the radius of the annular flange). A plane defining the loop of the second end of the bracket arm may be parallel to an axis of the head, the shank and the annular flange.

These and other features of the present subject matter will become readily apparent upon further review of the following specification.

BRIEF DESCRIPTION OF THE DRAWINGS

FIG. 2B is a top view of a collar and bracket arm of the bony screw with a movable bracket arm.

Similar reference characters denote corresponding features consistently throughout the attached drawings.

DETAILED DESCRIPTION OF THE PREFERRED EMBODIMENTS

Figure 1:
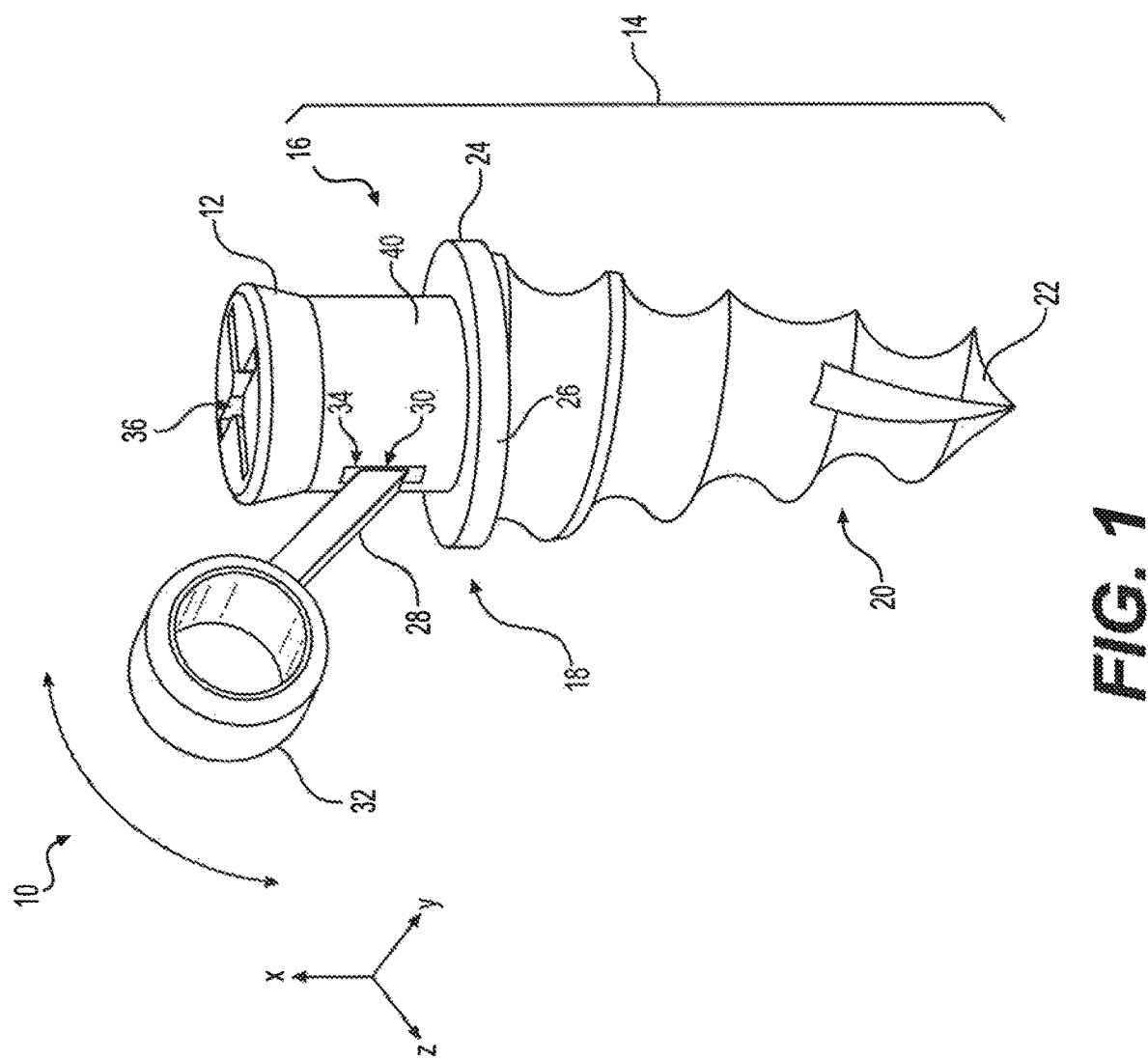
FIG. 1 is a perspective view of a bony screw with a movable bracket arm.
Figure 2A:
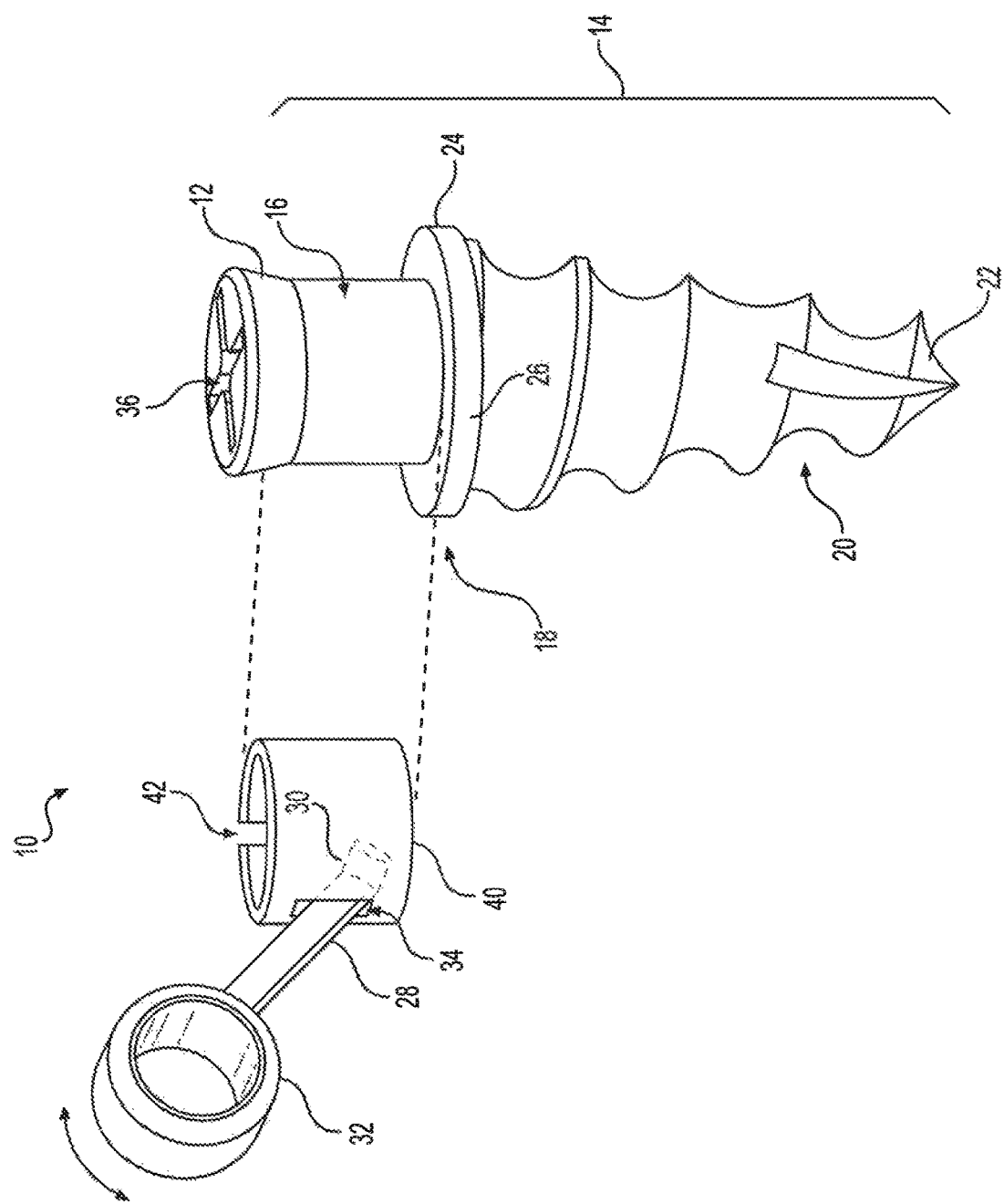
FIG. 2A is a partially exploded perspective view of the bony screw with a movable bracket arm.

A bony screw with a movable bracket arm 10 is provided for supporting a distractor or other maxillofacial fixing and dental appliance. The bony screw with a movable bracket arm 10 includes a head 12 and a tooth shank 14 extending therefrom. As a non-limiting example, in order to facilitate fixation, the head 12 may have cruciform slots defined therein; i.e., the head 12 may be a Phillips head, as shown in FIGS. 1 and 2A. However, it should be understood that head 12 is shown for exemplary purposes only, and may have any suitable type of slots or the like for fixation of bony screw with a movable bracket arm 10 and, similarly, may have any suitable contouring and relative dimensions.

As shown in FIG. 1, the shank 14 includes an upper portion 16, a threaded lower portion 20, adjacent to upper portion 16 (with a junction 18 defined therebetween), and a self-tapping tip 22 extending from the threaded lower portion 20. It should be understood that the overall contouring and relative dimensions of shank 14 are shown for exemplary purposes only. Further, it should be understood that the bony screw with a movable bracket arm 10 may be made from any suitable type of noncorrosive, biocompatible material. As a non-limiting example, the components of the bony screw with a movable bracket arm 10 may be made from stainless steel.

An annular flange 24 is disposed at the junction 18 between the upper portion 16 and the threaded lower portion 20 of shank 14. The annular flange 24 is contiguous with respect to each of the upper portion 16 and the threaded lower portion 20, and has a peripheral surface 26 with a diameter greater than a diameter of the head 12 and greater than a diameter of the upper portion 16, thus defining a stop between upper portion 16 and threaded lower portion 20. The stop defined by annular flange 24 prevents the bony screw with a movable bracket arm 10 from passing too deeply through the mucoperiosteum when fixing the bony screw with movable bracket arm 10 to the bone.

A first end 30 of a bracket arm 28 is pivotally secured to the upper portion 16 of the shank 14, and an opposed second end 32 of the bracket arm 28 defines a loop adapted for supporting a distraction osteogenesis bar or any other suitable type of maxillofacial or dental fixing appliance. In order to properly position and support the bar, or other maxillofacial fixing and dental appliance, the second end 32 of the bracket arm 28 may extend beyond the peripheral surface 26 of the annular flange 24 (i.e., the radial component of the length of the bracket arm 28 is greater than the radius of the annular flange 24). A plane defining the loop of the second end 32 of the bracket arm 28 may be parallel to an axis of the head 12, the shank 14 and the annular flange 24. In other words, in the example of FIG. 1, the looped second end 32 lies in the x-z plane, which is parallel to the overall axis of bony screw with movable bracket arm 10 (i.e., the x-axis). Thus, when a bar is received through the looped end 32, it will extend orthogonally to the x-axis.

As discussed above, the first end 30 of bracket arm 28 is pivotally attached to upper portion 16. In the exemplary coordinate system of FIG. 1, the looped second end may be angularly adjusted in the x-z plane. It should be understood that first end 30 may be pivotally attached to upper portion 16 using any suitable type of pivotal connection. In the non-limiting example of FIGS. 1-2B, a collar 40 is provided for pivotally securing bracket arm 28 to upper portion 16. As best shown in FIG. 2A, collar 40 has a slot 34 formed therethrough. In the non-limiting example of FIGS. 2A and 2B, first end 30 of bracket arm 28 is shown defining a short cylindrical rod having a length greater than the width of slot 34, thus securing the first end 30 within the collar 40. The second end 32 of bracket arm 28 is disposed external to the collar 40 such that the bracket arm 28 projects through the slot 34, as shown. When the collar 40 is secured about the upper portion 16 of the shank 14, as shown in FIG. 1, the first end 30 of the bracket arm 28 is pivotally secured between the collar 40 and the upper portion 16 of shank 14. Returning to FIG. 2A, as shown, an axial slot or gap 42 may be axially formed through the wall defining collar 40, allowing it to be easily attached about the upper portion 16 of shank 14. It should be understood that first end 30 may define any suitable shape, such as the short cylindrical rod, a rolled cylindrical sheet or the like, which remains within the interior of collar 40 and cannot accidentally pass through slot 34.

Figure 3:
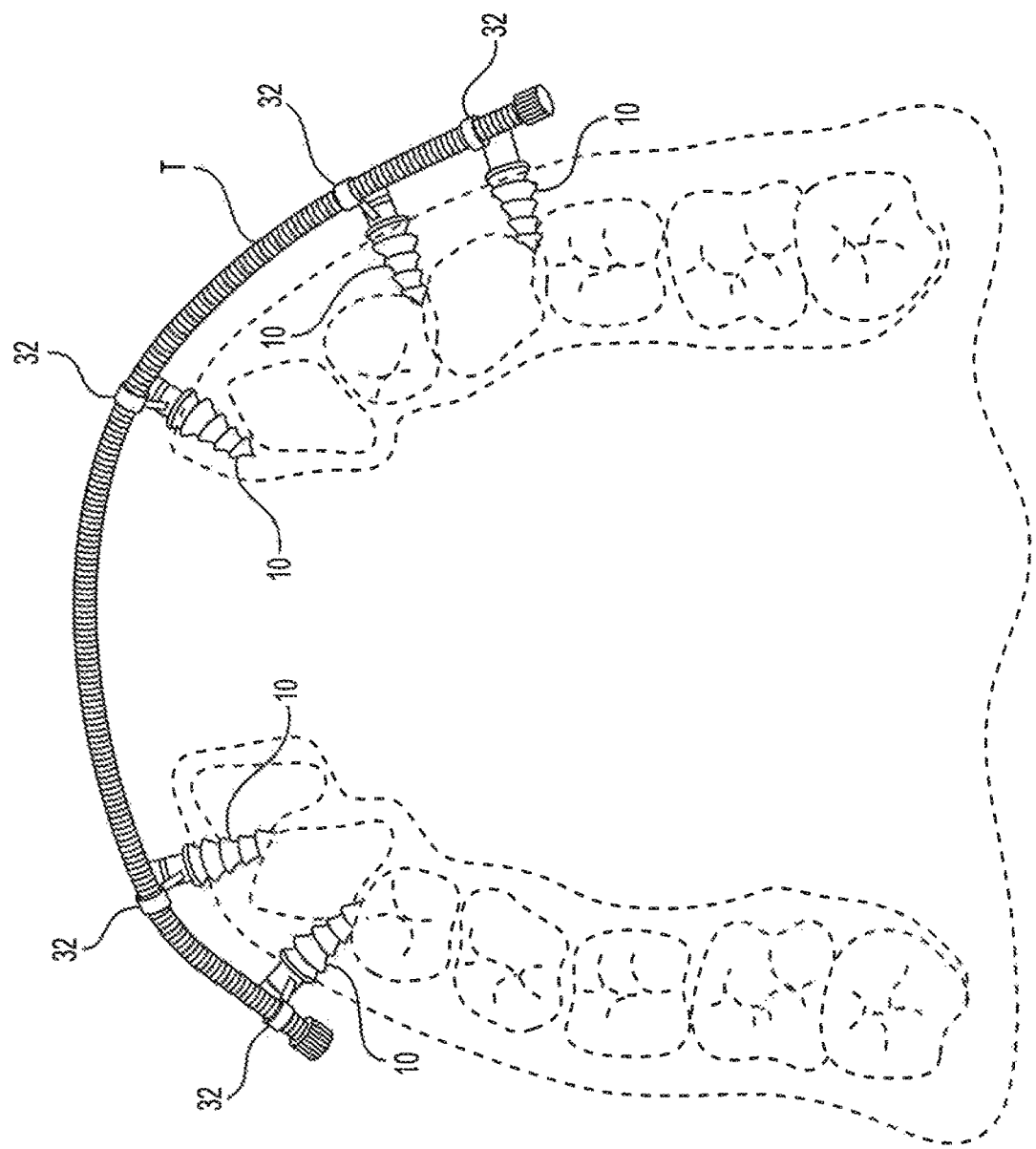
FIG. 3 is an environmental top view of an anterior curved distractor secured to the maxilla, or upper jaw, of a patient's mouth by a plurality of the bony screw with movable bracket arms of FIG. 1.

FIG. 3 illustrates an exemplary usage for bony screw with a movable bracket arm 10, with multiple ones of the bony screw with a movable bracket arm 10 being used to support an exemplary traction bar T of an anterior curved fixing bar or distraction device. The pivotal attachment of bracket arm 28 to upper portion 16 of shank 14 allows for adjustment of the bracket, thus easing passage of traction bar T through the looped ends 32 when the screws 10 are fixed to the bone at differing levels around the dental arch.

Exemplary representative dimensions of the bony screw with movable bracket arm 10 include an axial length of at least 12 mm and a thickness of about 2 mm. The length of the threaded lower portion 20 of the shank 14 may be at least 6 mm. The bracket arm 28 may be provided in different lengths to offset the looped second end 32 at different distances or heights, depending on the application. Exemplary representative lengths of the bracket arm 28 include a length approaching 0 mm, 2 mm, or 4 mm. The looped second end 32 may have an outer diameter of about 4 mm and a thickness of about 2 mm, defining a bore having an inner diameter of 2 mm. An exemplary thickness for collar 40 may be 0.5 mm. The annular flange 24 may have a diameter of 4 mm and a thickness of 1 mm. The threads of the threaded lower portion 20 of the shank 14 may have a pitch of 1 mm. It will be understood that the recitation of dimensions herein is provided for purposes of enablement, and not by way of limitation. Actual dimensions are a manufacturing detail, and may vary from the dimensions recited herein.

It should be understood that the bony screw with a movable bracket arm 10 can be used in conjunction with not only the exemplary traction bar T, but also with any type of distractor device, maxillofacial fixing device. The screws 10 may be fixed to the bone under local anesthesia, and provide a strong support for distraction devices and other dental appliances that can be installed and removed more quickly and easily than existing devices.

It is to be understood that the bony screw with a movable bracket arm is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A bony screw with a movable bracket arm, comprising:
    a head;
    an elongated shank extending from the head, the elongated shank defining a longitudinal direction, wherein the shank has an upper portion, a threaded lower portion adjacent to the upper portion thereby defining a junction, and a self-tapping tip extending from the threaded lower portion;
    an annular flange disposed at the junction between the upper portion and the threaded lower portion of the shank, the annular flange being contiguous with respect to each of the upper portion and the threaded lower portion, the annular flange having a peripheral surface and a diameter greater than a diameter of the head and greater than a diameter of the upper portion to define a stop between the upper portion and the threaded lower portion;
    a collar having first and second slots formed about its peripheral surface, the first slot being formed entirely through the collar whereby the upper portion of the shank is adapted to extend through the slot and be secured to the collar, the second slot extending vertically within the collar thereby forming upper and lower edges; and
    a bracket arm having opposed first and second ends, the first end being disposed within the second slot of the collar and pivotally secured solely in a vertical plane between the collar and the upper portion of the shank, the second end being disposed external to the collar and defining a loop adapted for supporting a maxillofacial or distraction osteogenesis bar.

2. In combination, a distraction osteogenesis bar and a plurality of elongated bracket screws therefore, comprising:
    the distraction osteogenesis bar, wherein the distraction osteogenesis bar is configured and dimensioned for maxillofacial fixing;

each of the plurality of elongated bracket screws comprising:
a head;
a shank extending from the head, the shank having an upper portion, a threaded lower portion adjacent to the upper portion thereby defining a junction, and a self-tapping tip extending from the lower portion, wherein the head and the shank define a longitudinal axis;
an annular flange disposed at the junction between the upper portion and the threaded lower portion of the shank thereby being contiguous to each of the upper portion and the threaded lower portion, the annular flange having a peripheral surface and a diameter greater than each of the head and the upper portion thereby forming a stop between the upper portion and the threaded lower portion;
a collar having first and second slots formed about its peripheral surface, the first slot being formed entirely through the collar whereby the upper portion of the shank is adapted to extend through the slot and be secured to the collar, the second slot extending vertically within the collar thereby forming upper and lower edges;
a bracket arm having opposed first and second ends, the first end being disposed within the second slot of the collar and pivotally secured solely in a vertical plane between the collar and the upper portion of the shank, the second end being disposed external to the collar and defining a loop adapted for supporting a maxillofacial or distraction osteogenesis bar; and
a retainer at the other end of the bracket arm, the retainer defining a bore adapted for supporting the distraction osteogenesis bar therein, the bore having a longitudinal axis, wherein the retainer extends beyond the peripheral surface of the annular flange, further wherein the longitudinal axis of the bore extends perpendicular to the longitudinal axis of the head and shank,
wherein the distraction osteogenesis bar extends through each of the bores of each of the retainers.

\* \* \* \* \*